(12) United States Patent
Stigsson et al.

(10) Patent No.: US 9,221,869 B2
(45) Date of Patent: Dec. 29, 2015

(54) RECOVERY OF PHYTOSTEROLS FROM RESIDUAL VEGETABLE OIL STREAMS

(75) Inventors: Lars Stigsson, Bjärred (SE); Valeri Naydenov, Luleå (SE)

(73) Assignee: SUNPINE AB, Pitea (SE)

( * ) Notice: Subject to any disclaimer, the term of this patent is extended or adjusted under 35 U.S.C. 154(b) by 331 days.

(21) Appl. No.: 12/921,610

(22) PCT Filed: Feb. 10, 2009

(86) PCT No.: PCT/SE2009/000076
§ 371 (c)(1),
(2), (4) Date: Dec. 2, 2010

(87) PCT Pub. No.: WO2009/113935
PCT Pub. Date: Sep. 17, 2009

(65) Prior Publication Data
US 2011/0082307 A1  Apr. 7, 2011

Related U.S. Application Data

(60) Provisional application No. 61/064,500, filed on Mar. 10, 2008.

(51) Int. Cl.
*C07J 9/00* (2006.01)
*C11C 3/00* (2006.01)
*C11C 3/04* (2006.01)

(52) U.S. Cl.
CPC . *C07J 9/00* (2013.01); *C11C 3/003* (2013.01); *C11C 3/04* (2013.01)

(58) Field of Classification Search
USPC .......................................... 552/541; 514/170
See application file for complete search history.

(56) References Cited

U.S. PATENT DOCUMENTS

| | | | |
|---|---|---|---|
| 2,280,843 A | 4/1942 | Oliver et al. | |
| 2,715,638 A | 8/1955 | Albrecht et al. | |
| 2,715,639 A | 8/1955 | Albrecht et al. | |
| 2,835,682 A | 5/1958 | Steiner et al. | |
| 3,691,211 A * | 9/1972 | Julian | 552/545 |
| 3,803,114 A * | 4/1974 | Mitchell et al. | 530/205 |
| 3,840,570 A | 10/1974 | Julian | |
| 3,887,537 A * | 6/1975 | Harada et al. | 530/208 |
| 3,965,085 A * | 6/1976 | Holmbom et al. | 530/208 |
| 4,151,160 A * | 4/1979 | Koebner | 530/209 |
| 4,526,231 A * | 7/1985 | Radke | 166/270.1 |
| 5,627,289 A * | 5/1997 | Jeromin et al. | 549/413 |
| 6,057,462 A * | 5/2000 | Robinson et al. | 552/545 |
| 6,297,353 B1 * | 10/2001 | Fuenzalida Diaz et al. | 530/205 |
| 7,087,402 B2 * | 8/2006 | Diaz et al. | 435/52 |
| 8,318,962 B2 * | 11/2012 | Kang et al. | 552/545 |
| 8,338,564 B2 * | 12/2012 | Wong et al. | 530/205 |
| 2004/0024175 A1 * | 2/2004 | Wong et al. | 530/230 |
| 2005/0010061 A1 * | 1/2005 | Hamunen | 552/540 |

FOREIGN PATENT DOCUMENTS

| | | |
|---|---|---|
| CA | 2 349 780 C | 3/2009 |
| WO | 99/42471 A1 | 8/1999 |
| WO | 00/64921 A2 | 11/2000 |
| WO | 03/022865 A1 | 3/2003 |
| WO | 2004/080942 A1 | 9/2004 |
| WO | 2007/050030 A1 | 5/2007 |

OTHER PUBLICATIONS

Comparative study of 1.132 declaration.*
Supplementary European Search Report, completed Jun. 25, 2012; Appln. No. EP 09 71 9905.
P. Fernandes, et al; "Phytosterols: Applications and recovery methods", In: Bioresource Technology, 2007, vol. 98, pp. 2335-2350, pp. 2342-2345, figure 6.
International Search Report PCT/SE2009/000076.

* cited by examiner

*Primary Examiner* — Sabiha N Qazi
(74) *Attorney, Agent, or Firm* — Ladas & Parry LLP

(57) ABSTRACT

There is disclosed a method for isolation and purification of phytosterols from tall oil pitch comprising the steps of: a) contacting the tall oil pitch with a solvent to form a tall oil solvent mixture; b) separating the tall oil pitch solvent mixture in at least two separate streams wherein one process stream is enriched in acidic pitch components and a second stream enriched in free- and bound sterols in the form of steryl esters; c) subjecting the stream enriched in free- and steryl esters to treatment with an alcohol under transesterification conditions wherein a reaction mixture is formed and sterols comprising the steryl esters are liberated as free sterols; and d) separating the free sterols from the reaction mixture of step c) by crystallization and extraction with one or more solvents. There are disclosed free fatty acids and resin acids separated from the tall oil pitch. Moreover, there is disclosed a manufacture and separation of fatty acid alkyl esters by the method.

16 Claims, 1 Drawing Sheet

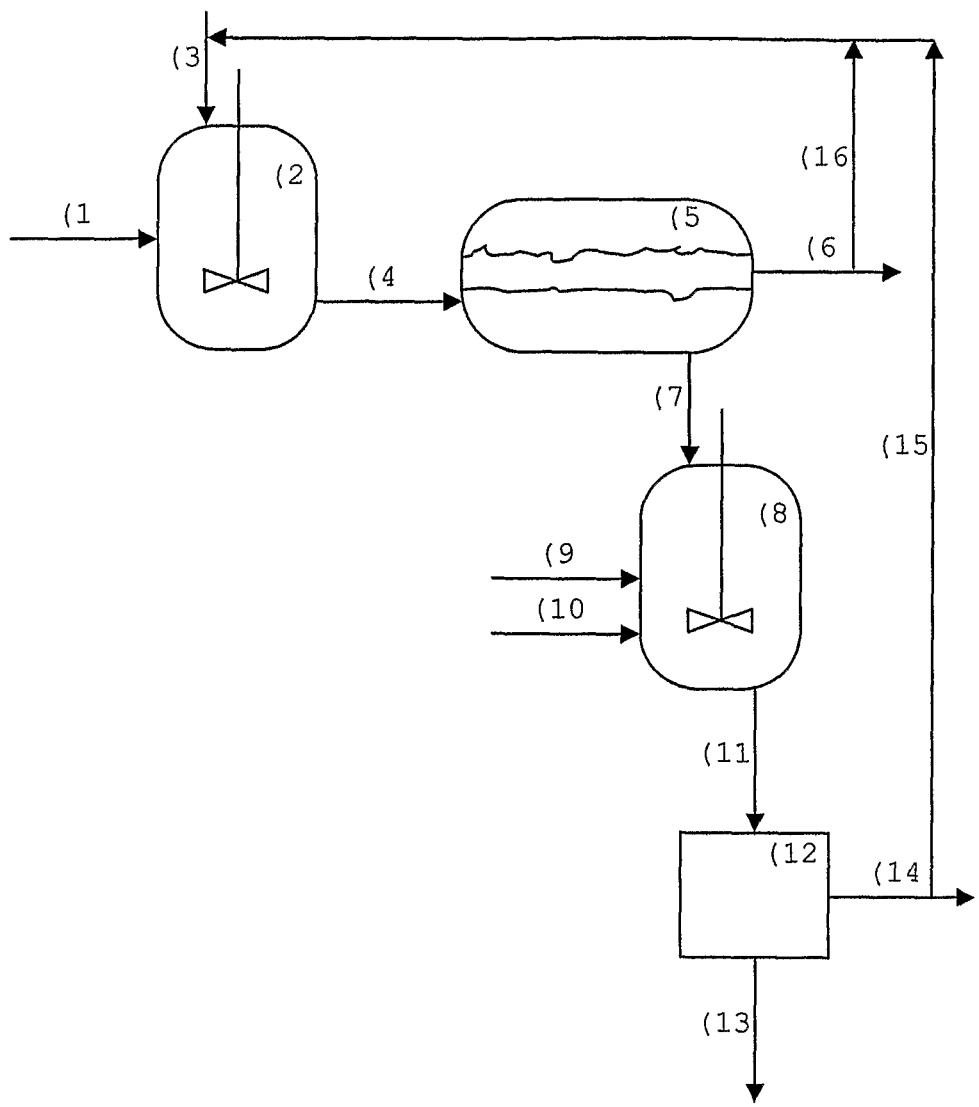

RECOVERY OF PHYTOSTEROLS FROM RESIDUAL VEGETABLE OIL STREAMS

TECHNICAL FIELD

The present invention relates to a method for isolation and purification of phytosterols from Tall Oil Pitch (TOP) and other phytosterol-rich materials and more particularly relates to the isolation and purification of beta-Sitosterol from such sources. The present invention further relates to Free Fatty Acids (FFA), Fatty Acid Alkyl Esters (FAAE) and Resin Acids (RA) formed in said method.

BACKGROUND

The term phytosterol refers to a group of compounds, which are naturally occurring in plants. In the recent years, there has been a growing interest in these compounds due to their wide range of applications such as food and cosmetic additives as well as active component in various pharmaceutical formulations. An area, which is gaining special interest in the past few years and which additionally increases the demand for phytosterols and their derivatives, is the area of so called functional foods where the active substance has cholesterol-lowering effect upon scheduled use. It has been proven that plant sterols and their derivatives reduce cholesterol levels in human blood.

The compounds within phytosterol group comprise one of the two branches of a larger steroid group. The other branch of steroid group is comprised of compounds found in humans and animals with typical example being cholesterol. Steroids are terpenoid lipids characterized by carbon skeleton which is comprised typically of four fused rings (most often in 6-6-6-5 fashion, where numbers 6 and 5 denote the number of carbon atoms in each ring). Most often, each ring within the fused ring structure is denoted by a capital letter, thus the four fused rings structure is often written as A-B-C-D, where D corresponds to cyclopentane-ring. There are hundreds of steroid members known and characterized, where the main difference is in their functional groups. When hydroxyl (—OH) functionality is attached to the ring skeleton (usually to the $3^{rd}$ carbon atom in the A-ring), the steroids are referred to as sterols. All phytosterols are based on the cycloartenol-type sterol, whereas all animal steroids are based on the lanosterol-type sterol.

Generally, the phytosterols are concentrated and isolated during vegetable oil processing where both edible and non-edible oils can be considered as potential candidates for phytosterol source. Thus, all crops utilized for vegetable oil production can be used as phytosterol sources, where typical examples include but not limited to oils obtained from soybean, canola, corn, cottonseed, palm, etc. The phytosterols in vegetable oils are present in free form and/or as steryl esters (SE, esters formed between corresponding phytosterol and fatty acid), where the total phytosterol content is typically in the range of up to one percent by weight. During the vegetable oil refining, residual streams enriched in phytosterols can be obtained and used as sources for subsequent sterol isolation.

An alternative source for phytosterols is Tall Oil (TO) a non-edible vegetable oil, which is a by-product product available at the pulp and paper mills. The tall oil is comprised of lipophilic extractives of wood. During wood cooking (typically via Kraft-type process) these extractives are solubilised into the cooking liquor through alkali assisted hydrolysis. Thus obtained cooking liquor is concentrated further in series of evaporation steps. At certain concentration, the solubilised lipophilic components naturally separate from the remaining aqueous phase and are skimmed-off from the liquor. The obtained stream is often referred to as tall oil soap or just soap. The tall oil soap typically is acidulated at the mill sites to obtain an oil phase, tall oil, and a brine aqueous solution. The obtained TO or more often referred to as crude tall oil (CTO), is typically exported to centralized tall oil refineries for further upgrading.

The CTO is comprised of an acidic fraction and a neutral fraction. The acidic fraction is further sub-divided into free fatty acids (FFA, 35-60 wt. %) and resin acids (RA, 15-55 wt. %), where the components of both fractions are characterized by the presence of carboxylic acid functionality (—COOH). The neutral fraction (5-35 wt. %) on the other hand, is comprised of a large number of compounds such as alcohols, aldehydes, ketones, hydrocarbons, etc. The common feature for these compounds is that they are not prone to reaction with alkali and hence often referred to as unsaponifiables. The phytosterol-type components dominate within the TO neutral fraction and beta-Sitosterol is the principal component of the neutral fraction. Further, the phytosterols are present in tall oil mainly as free sterols because of the hydrolysis conditions during the wood cooking. Nevertheless, some steryl esters can be also found in TO, where the amount of steryl esters is mainly dependent on the tall oil origin, pre-treatment and storage conditions.

Tall oil upgrading typically involves one or more vacuum distillation steps, where the objective is to obtain the two principal component fractions, namely those of free fatty acids and resin acids. Upon their removal, a high boiling-point fraction remains as bottom stream which is enriched in phytosterols and is usually referred to as Tall Oil Pitch (TOP) or just pitch. The obtained TOP is typically used as low cost energy source at various industrial sites. In light of phytosterol isolation, the tall oil pitch is preferred source over the initial tall oil due to the reduced volumes to be processed. Typical sterols present in TO and respectively in TOP include beta-Sitosterol, Stigmasterol, Campesterol, though their saturated counterpart's beta-Sitostanol, Stigmastanol, Campestanol, respectively can be found also in minor quantities.

Over the years many processes have been developed for phytosterol isolation from by-product streams within Pulp & Paper industry. Depending on the stream enriched in phytosterols, different strategies have been adopted.

Although the preferred source stream for sterol isolation is TOP, some process disclosures on previous art describing sterol isolation from tall oil soap and TO streams have to be mentioned, since the ground principles within these disclosures are applied often at certain process stage within the tall oil pitch upgrading.

Soap stream is attractive source for phytosterol isolation because the major fraction i.e. acidic fraction is in the salt form, typically sodium salts whereas the neutral fraction containing the sterols is not affected by the alkali. Further, all phytosterols are present into the soap stream are already as free phytosterols. The U.S. Pat. No. 3,965,085 and U.S. Pat. No. 3,803,114 describe similar strategies for the isolation of neutral fraction from soap streams available at the Pulp & Paper mills. The common feature for these processes is the use of hydrocarbon-based solvent to extract the neutral fraction whereas the acidic fraction of the soap remains in the aqueous phase. In order to facilitate the separation and prevent the formation of stable emulsions auxiliary solvent is introduced into the system, ketone or low-molecular weight alcohol as described in U.S. Pat. No. 3,965,085 and U.S. Pat. No. 3,803,114 respectively. Although demonstrated on commercial scale, the processes have many disadvantages which can be summarized as: (i) large volumes to be processed; (ii) need for large volumes of solvents used within the extraction step; (iii) need of high quality soap (essentially free of black liquor) otherwise extensive problems with phase separation between soap (aqueous) and hydrocarbon based solvent phases; (iv) need for solvent recovery loops (minimum two solvents are utilized); (v) need for further phytosterol isolation from the other neutral components extracted from the soap; etc.

Phytosterol isolation has been demonstrated on TO streams as well. The phytosterols within TO stream are mainly as free sterols but certain amounts of steryl esters are also found. The amount of steryl esters depends on the TO origin, pre-treatment conditions as well as storage conditions and duration.

U.S. Pat. No. 2,280,843 discloses a process for the preparation of sterol concentrate from TO. The TO stream is dissolved in suitable solvent and the obtained common stream is passed through a bed of appropriate sorbent which retains the neutral fraction of the TO. The retained neutrals can be liberated by passing through the adsorbent bed different type of solvent in which neutrals are readily soluble. Eluted neutral fraction is concentrated by means of solvent evaporation to render neutral oil from where the sterols can be isolated in an additional step.

WO 2004/080942 discloses a process for the CTO fractionation into FAAE's, RA's and sterol streams. In this process, the TO is modified first by means of selective esterification of FFA with alkyl alcohol to the corresponding FAAE's, followed by sterol esterification with boric acid to obtain the corresponding sterol borate esters. The modified tall oil is fractionated via vacuum distillation to obtain sterol borate ester concentrate, which is used to isolate the free sterols via hydrolysis of borate esters.

CA 2349780 discloses a process for the sterol isolation from TO stream. In this process, the initial CTO is distilled to remove the light oil fraction, containing the FFA's and RA's, and the residue containing the sterols. The residue is further fractionated into a distillate containing concentrated free sterols and a high boiling point residue. The sterols are isolated from the sterol concentrated distillate via crystallization in suitable solvents.

The process disclosures on phytosterol isolation from tall oil have many disadvantages similar to the case of tall oil soap: (i) large volumes to be processed are involved; (ii) the use of number of solvents is involved; (iii) heavy distillation conditions are involved, in certain cases a number of distillation steps are needed; (iv) in most of the cases the steryl esters or in more particular the sterols within these esters are not recovered which may substantially decrease the total sterol yield.

From commercial point of view, the tall oil pitch is particularly interesting since the phytosterols and their derivatives are most concentrated. A number of processes have been disclosed on the phytosterol isolation from TOP. However, the state of phytosterols in the TOP differs significantly from the one in tall oil soap and tall oil. In the TOP phytosterols are present typically as steryl esters and only minor amounts of free sterols. The presence of phytosterols in the form of steryl esters to large extent predetermines the possible processing schemes for phytosterol isolation from TOP.

WO 99/42471 discloses a process where the sterols are isolated from TOP by complete saponification of the TOP to obtain the FFA's and RA's in their alkali salt forms and liberate the bound sterols. The obtained soap phase is acidulated to obtain TO enriched in sterols, which is further distilled to obtain a light volatile distillate fraction comprised of FFA's and RA's and a residue fraction. The residue fraction is subsequently distilled to obtain sterol concentrate, which in turn is used for the sterol isolation by applying suitable solvents.

U.S. Pat. No. 2,715,638 and U.S. Pat. No. 3,691,211 disclose similar processes for sterol isolation from TOP. The acidic fraction of the TOP is neutralized with water-alcoholic alkali solution. The separation of the soap phase and the oil phase in some cases is facilitated by addition of auxiliary non-polar solvent as described in the U.S. Pat. No. 3,691,211. The soap phase is discarded, whereas the oil phase containing bound sterols is subjected to hydrolysis conditions where the steryl esters are hydrolyzed to free sterols and corresponding alkali salts of the FFA's. Upon cooling the sterols crystallize and can be separated.

The U.S. Pat. No. 2,715,639 discloses a process for sterol isolation from TOP via direct saponification of the TOP water-alcohol alkali solution. The obtained soap phase is diluted with large amount of water and allowed to cool-down. Upon cooling the sterols crystallize and can be separated.

The WO 00/64921 discloses a process for sterol isolation and purification from TOP. The TOP is first completely saponified to hydrolyze all steryl esters to free sterols and FFA's. The neutral fraction of TOP is extracted by art similar to the one described for extraction of tall oil soap. The obtained neutral fraction is further upgraded to phytosterols of high quality through preparation of sterol-metal aducts, which are separated and subsequently hydrolyzed to obtain free sterols.

There are number of disadvantages concerning the process disclosures on phytosterol isolation from tall oil pitch which can be summarized as: (i) the use of alkali treatment step typically complete saponification of TOP; (ii) generation of an additional soap streams that typically need to be acidulated to produce an oil stream; (iii) use of heavy distillation conditions to further concentrate the sterols and (iv) the use of large volumes of solvent mixtures to concentrate and/or isolate the sterols.

Although, the residual streams which have potential for phytosterol isolation can differ significantly in their bulk matrix composition, the main criteria for selection of isolation procedure is the sterol state i.e. whether the major sterol fraction is comprised of free sterols or steryl esters—bound sterols. There is an obvious need for universal procedure for phytosterol recovery which (i) allows the isolation of phytosterol fraction of high quality and high yield (ii) is independent of the particular characteristics of the source stream (free sterols and/or steryl esters) and (iii) that eliminates most and preferably all of the disadvantages of existing practices for phytosterol recovery listed earlier.

In the following we describe a process for isolation of phytosterol fraction from tall oil pitch in high quality and yield. Furthermore, we believe that because of its universal philosophy, the process can be adapted to any type of residual stream concentrated in phytosterols.

SUMMARY OF THE PRESENT INVENTION

The main objective of the present invention is to recover and upgrade tall oil pitch to high value phytosterols. It is furthermore an objective to provide a universal process for phytosterol isolation and purification in higher yields than the prior art. A further objective is to provide an efficient method for recovering the free fatty acids, bound fatty acids in steryl esters and the resin acids present into the tall oil pitch. Moreover, there is provided a fatty acid alkyl ester manufactured with the method according to the present invention.

The present invention discloses an innovative sequence of separation and reaction steps enabling the production of phytosterols from tall oil pitch in high yield. The high yield of phytosterols is attained by recovering both free and bound sterols. Other valuable chemicals such as free fatty acids, resin acids and fatty acid alkyl esters can be recovered along the procedure described in the present invention.

The present invention thus provides a method for phytosterol isolation from tall oil pitch comprising the steps of: a) contacting the TOP with a solvent at elevated temperatures and under intense agitation, where enabling maximum contact between the solvent and the TOP or complete dissolution of the TOP in the solvent; b) allowing the mixture to separate under cooling, thus forming two process streams (i) a stream containing the acidic pitch components such as free fatty acids and resin acids and (ii) a modified tall oil pitch stream containing both the bound sterols and the free sterols; c) subjecting the modified tall oil pitch stream containing all sterols to conditions promoting transesterification of steryl esters in presence of alkali catalyst and C1 to C8 alkyl alcohol to form fatty acid alkyl esters and additional fraction of free sterols; d) allowing the reaction mixture to mature at cooling conditions upon which the sterol fraction crystallizes; e) separating the formed sterol crystals from the oil stream enriched in fatty acid alkyl esters.

According to one specific embodiment of the present invention, there is provided a method for recovering phytosterols from tall oil pitch (TOP) by a sequence of reaction and separation steps, wherein the method comprises the steps of:
  a) contacting TOP with a solvent at a temperature above 25 degrees C. thereby forming a TOP solvent mixture;
  b) separating the TOP solvent mixture into at least two separate process streams or phases wherein a first process stream or phase is enriched in acidic pitch components and a second process stream or phase is enriched in free sterols and bound sterols in the form of steryl esters;
  c) subjecting the second process stream or phase enriched in free sterols and steryl esters to treatment with at least one alcohol and at least one catalyst thereby forming a reaction mixture wherein at least a portion of the steryl esters is liberated as free sterols; and
  d) separating free sterols from the reaction mixture of step c).

Step c) above comprises the liberation of the sterol-part of the steryl ester molecules into free sterols. When step c) is performed via transesterification, a new fatty acid alkyl ester is formed between fatty acid comprising the steryl ester molecule and the corresponding alcohol and simultaneously the liberation of free sterol occurs. As may be noted from above, according to one specific embodiment of the present invention, step c) is achieved by a transesterification.

However, another possible reaction type for step c), for generating liberation of free sterols, is hydrolysis. In this case an alkali catalyst is used.

Further embodiments of the present invention are described in the following description and the appended dependent claims.

DESCRIPTION OF THE DRAWING

FIG. 1 shows one embodiment of sterol concentration and isolation of the present invention.

In the particular embodiment described in FIG. 1, the preheated tall oil pitch (1) is charged into stirred reactor (2). Methanol (3) spiked with water up to (10%) is injected in the reactor (2) in amount 1:1 relative to the TOP (1). The methanol (3)-TOP (1) mixture is kept at the elevated temperature and vigorously agitated to ensure maximum contact between the TOP (1) and Methanol (3). The homogenized mixture (4) is transferred into vessel (5) where it is allowed to cool-down and separate. The polar components of the TOP are concentrated into the top layer comprised of methanol-water solvents. The polar fraction of tall oil pitch is removed through stream (6) comprised mainly of free fatty acids, resin acids and other oxidized products formed during the tall oil fractionation at the tall oil distilleries. The top layer (6) is continuously removed from separation vessel (5). The solvents comprising stream (6) are recovered and returned via (7) to the methanol-water stock for re-use as solvent stream (3). The sterols and steryl esters are concentrated in the bottom layer (8), which is continuously discharged from the separation vessel (5) and charged into CSTR (9). The stream (8) is characterized by low acid value (AV) about 1.0 mg KOH or bellow. The stream (8) is combined with sodium methoxide (10) in amount corresponding to the molar ratio steryl esters:methanol=1:10 and sodium hydroxide up to 1.0 wt. % on steryl ester basis. The two streams are reacted at reflux conditions under vigorous agitation to convert essentially all steryl esters to fatty acid methyl esters and free sterols. The reaction mixture is discharged from the CSTR (9) as stream (11) and allowed to cool-down, vessel (12). Upon cooling sterols crystallize and are filtered-off and the filter cake comprised of crude sterol is isolated (13). The fatty acid methyl ester enriched stream (14) is subjected to solvent recovery where methanol is separated and combined with the methanol-water stock for re-use as stream (3). The stream enriched in fatty acid methyl esters is directed for further processing to obtain FAME stream of high quality.

It is to be understood that this invention is not limited to the particular embodiment shown above. The scope of the present invention is limited only by the appended claims and equivalents thereof.

DETAILED DESCRIPTION OF THE INVENTION

The inventors of the present invention have discovered a new and efficient method for the isolation of phytosterols of high purity and in high yield from tall oil pitch. In addition, valuable by-product streams comprised of resin and free fatty acids as well as stream enriched in fatty acid alkyl esters are recovered.

The feedstock material of the present invention is tall oil pitch obtained during tall oil upgrading at tall oil distillery plants. The tall oil upgrading is done in a series of vacuum distillation steps where typically the volatile fraction is removed first from the high-boiling point fraction. The volatile fraction is comprised of free fatty and resin acids and is subjected to further upgrading to obtain the two principle acid-types in separate streams. The high-boiling point fraction from tall oil distillation is the so called tall oil pitch, which corresponds to 15-40 wt. % on the CTO and depends mainly on the tall oil origin, composition and to large extent on the operating conditions during the upgrading.

The typical tall oil pitch is comprised of free fatty acids 10-15 wt. %, 5-12 wt. % resin acids, about 15 wt. % low molecular weight neutrals and about 35 wt. % high molecular weight material. Fractions of about 1-3 wt. % of fatty acids and resin acids are present as esters. The low molecular weight neutrals are comprised of fatty alcohols C20-C24 and phytosterols. The most important feature of the low-molecular weight neutrals is that they are found in the form corresponding steryl esters (phytosterol-fatty acid ester) and wax-type esters (fatty alcohol-fatty acid ester). Further, only about 5 wt. % of phytosterols present the tall oil pitch are as free phytosterols with remaining part of phytosterols are bound sterols in the form of steryl esters. The steryl esters are formed during the tall oil drying, storage and upgrading.

The tall oil is subjected to drying treatment (elevated temperatures up to above 100 degrees C. and often moderate vacuum) which removes the last amounts of brine entrained into the oil during tall oil soap acidulation. Further, the CTO is usually stored at elevated temperatures in order to prevent oil solidification and to facilitate its pump ability. The CTO distillation is performed at very high temperatures 200-300 degrees C. and strong vacuum 1-10 mbar conditions. It is to be noted that steryl esters are formed via esterification reaction. This reaction, in general, is an equilibrium reaction and hence any established equilibrium can be disrupted by alternation of temperature and/or removal of reaction product such is the reaction water. All conditions used within tall oil drying, storage and distillation favor the transformation of free phytosterols into steryl esters i.e. during the whole CTO processing-sequence (from preparation to final fractionation) steryl esters are produced and concentrated in the tall oil pitch. Most often the major fraction of steryl esters is generated during the tall oil distillation.

According to one specific embodiment of the present invention, the TOP is recovered from distillation of crude tall oil under vacuum at a maximum temperature below about 270 degrees C.

A substantial fraction of the tall oil pitch is the high molecular weight material (about 35 wt. %). The notation typically refers to various dimeric components formed through condensation reaction between two fatty acids or two resin acids. The condensation reactions typically take place during the TO upgrading at the tall oil distillery plants. An interesting feature of such dimmers is that they may retain their carboxylic groups and hence contribute for example to the total acidity of such sample.

The tall oil pitch contains also minor amounts of contaminants such as lignin fragments and inorganic salts (mainly sulphate-based). Both types of contaminants are retained in the oil phase during the tall oil production and follow the whole CTO processing sequence and are concentrated in the tall oil pitch.

Another type of tall oil pitch, which differs substantially from the TOP described above, can be obtained when practicing the procedure described in WO 2007/050030 A1 patent application incorporated herein in its entirety. In this process, the reactive carboxyl functionality (—COOH) of tall oil free fatty acids is "immobilized" through alkylation reaction with low molecular weight alcohol to the corresponding ester entity prior the tall oil fractionation. The formation of the fatty acid alkyl esters renders the fatty acids unavailable for esterification reactions with the phytosterols (typically during distillation stages of tall oil refining) and hence the phytosterols ending-up in the tall oil pitch are present as free sterols. Some bound sterols, formed during tall oil drying and storage can be also found in this type of TOP.

Tall oil pitch recovered in accordance with either of procedures described above is raw material fed into stirred reactor or reactors of the present invention. One objective within this first step of the process is to produce a modified pitch in which polar components initially present into the TOP and in particular components with carboxyl functionality (—COOH) are removed. Another objective of this process step is to further concentrate the free and bound sterols.

These objectives can be met by contacting the TOP with solvent which has affinity towards polar components whereas free sterols and bound sterols have limited or are not soluble in the said solvent. Such solvent can be selected from the group of low molecular weight alkyl alcohols such as methanol (C1), ethanol (C2), iso-propanol (C3), etc. up to octanol (C8). Preferably the alcohol is selected from methanol or ethanol. The free sterols are partially soluble in these alcohols whereas the steryl esters are practically insoluble in the C1 to C8 alcohols. The solubility of the free sterols in the C1-C8 alcohols increases with an increase in the number of carbon atoms i.e. from methanol (C1) towards octanol (C8). We have discovered that the desired solvent properties i.e. high affinity towards TOP polar components and incompatibility with free sterols and steryl esters can be tailored by adding certain amount of water to the selected alcohol. The amount of water may vary between 2-20 wt. % but preferably between 5-10 wt. % and most preferred are water quantities in the range 7.5-10 wt. % relative to the alcohol. Precise control over the water content ensures high efficiency and high selectivity of the solvent mixture towards the polar components of TOP and the presence of negligible quantities of free sterols and/or bound steryl esters. It should be noted that it is possible to use higher amounts of water (>20 wt. %) but the efficiency of the extraction relative to the polar components present into the TOP greatly decreases. Another consequence of using >20 wt. % water is related to the possibility of having the layer containing polar components as a bottom stream in vessel (5) instead as top layer as in the preferred embodiment of the present invention.

To sum up, according to one specific embodiment of the present invention, the solvent used in step a) comprises a C1-C8 alcohol. According to another specific embodiment, a major portion or all of the solvent used in step a) is a monohydric C1-C4 alcohol, such as methanol, or a mixture of different monohydric C1-C4 alcohols. Moreover, according to one embodiment, a major portion or all of the solvent used in step a) is a mixture of monohydric C1-C4 alcohol and water, such as a mixture of methanol and water, or mixtures of different alcohols and water.

The reactor (2) in FIG. 1 can be any process equipment that is able to provide a good contact between the tall oil pitch and the solvent. The good contact is essential in order to maximize the amount of TOP polar components transferred into the solvent phase. The good contact can be provided for example by means of ultra- and high-shear mixers in combination with baffles in various space configurations, ultrasound and microwave irradiation, etc. Another alternative to provide a good contact is to enhance the surface area where the TOP and solvent meet. Yet another alternative for providing a good contact is to perform the operation at elevated temperatures where the density of the TOP is substantially decreased and thus more compatible with the solvent. The temperature conditions in the reactor (2) are selected such that do not exceed the boiling point of the alcohol in cases when methanol, ethanol and iso-propanol are used. This requirement is dictated by practical (relating to safer conditions) and economical (related to the use of non-pressurized and hence cheaper equipment) reasons rather than process inapplicability. Thus the extraction of the polar components of TOP taking place in reactor (2) is performed at moderate conditions with respect to temperature i.e. well under 100 degree C., preferably at about 60 degrees C. in the cases when methanol is used as solvent.

To sum up, according to one specific embodiment of the present invention, TOP is contacted with the solvent in step a) under intense mixing at a temperature from 25 to about 250 degrees C. The temperature used is dependent on the solvent used, as is discussed above. The reactor used for step a) may be at least one continuous stirred tank reactor according to one specific embodiment of the present invention.

The tall oil pitch and the solvent are non-miscible at normal conditions. However, depending on the TOP composition and the amount of water used to spike the methanol solvent, at elevated temperatures and intensive mixing the mixture (4) coming out from reactor (2) can be as single-phase system. Nevertheless, upon cooling in vessel (5), two separate layers are always formed as depicted on the drawing. In the cases when other alcohols, other than methanol, are used for extraction, the probability for one phase system in stream (4) increases. However, the use of optimal amount of water to spike the alcohol and cooling always results in a sharp separation as shown on the drawing.

The separation of polar tall oil pitch components can be provided also in a mixer settler i.e. in a single process unit that combines the functions of reactor (1) and vessel (5). Mixer settlers are often used in solvent extraction processes. As the name suggests a mixer settler unit comprises of mixing stage/compartment followed by quiescent settling stage that allows phase separation by gravity. The mixing compartment provides possibilities for agitation at elevated temperatures and even can be pressurized (in cases when temperatures higher than the boiling points of solvent are utilized). Mixing section of a mixer settler may comprise of several mixing sub-sections where each of these sub-sections may be operated independently i.e. different mixing regimes are possible to be applied.

Therefore, according to one specific embodiment of the present invention, the contact of TOP with the solvent in step a) and the separation of TOP into two process streams or phases in step b) are performed in a mixer settler.

As is mentioned above, the affinity characteristics of the TOP may be used for achieving step b). Therefore, according to one specific embodiment of the present invention, a major portion of acidic pitch components comprising the TOP are separated based on their affinity towards polar solvents in step b). However, neutralization, adsorption, extraction, distillation or combinations thereof are also possible to use for the separation in step b), but these methods should be more demanding in terms of chemicals, energy, etc. Nevertheless, the object of this step is to remove the TOP acidity.

According to another specific embodiment of the present invention, the acidic pitch components of the TOP are separated by at least one extraction with solvent in steps a) and b).

The extraction of the polar components of the tall oil pitch may need to be done in several stages. The number of extractions depends on the effectiveness in removing the acidic components. The acid value of the modified TOP (7) should be about 10 mg KOH g$^{-1}$ preferably below 5 mg KOH g$^{-1}$ and most preferably about 1 mg KOH g$^{-1}$. Reaching the desired values for modified TOP (7) corresponds to separating tall oil pitch fraction in the order of about 30 wt. %. Therefore, the sterols and the corresponding steryl are concentrated into the modified TOP (7) since neither sterols nor the esters are soluble into the preferred solvent.

The production of modified TOP i.e. TOP depleted in acidic components can be achieved by performing the extraction in a counter-current fashion utilizing any commercial units designed for this type of extraction.

The acidity of the tall oil pitch can be decreased to the desired levels by other well known approaches such as neutralization and adsorption on appropriate sorbent. However, these two approaches require the use of additional equipment, chemicals, additional solvents, adsorbent media, etc. thus making them, as mentioned, less attractive options when practicing the process described in the present invention.

An important feature of the present invention should be described. This feature concerns the cases when the process is practiced on tall oil pitch obtained via art disclosed in WO 2007/050030 A1 patent application incorporated here in its entirety. The tall oil pitch in this case contains most of the phytosterols in their free form. As a consequence the sterols may crystallize within the bottom layer in the cold part of vessel (5). In such case, the sterols may be isolated from the liquid by any of the known methods for example decantation, filtration, centrifugation, etc. to obtain crude sterols and oil phase. The obtained crude sterols can be further purified to obtain the sterols of high purity. If the sterol yield is not satisfactory the tall oil pitch can be further processed according to the process depicted on FIG. 1. It should be noted that the presence of certain amount of crystallized sterols into the stream (7) does not cause any difficulties in handling the oil phase. Thus, the process described in the present invention can still be practiced although the crystallization of the free sterols in stream (7). Further, the sterols present in the TOP can be recovered in two portions first free sterols followed by the recovery of bound sterols or carrying-out the whole process regardless the crystallization of free sterols and recovering total sterols (free and bound) at the end of the process.

According to the present invention, there is a possibility where the crystallized free sterols within the second process stream or phase after step b) are already collected at this stage or perform all of the steps and collect these sterols as total sterols later on. Therefore, according to one specific embodiment of the present invention, free sterols that have crystallized within the second process stream or phase after step b) are separated from the second process stream or phase before step c).

The modified tall oil pitch (stream (7)) characterized by low acidity is pumped into a CSTR reactor where it is mixed with low molecular weight alcohol C1-C8 and an alkali catalyst. The alcohol is preferably methanol or ethanol. The use of higher alcohols is not an attractive option mainly due to economical reasons. The main objective of this treatment is to liberate the bound sterols present as steryl esters without demanding saponification treatment. Another objective is to provide the fatty acids comprising steryl esters in more suitable form for separation, in this case transforming them to FAAE's which are readily separated at mild distillation conditions.

The liberation of the bound sterols and the formation of FAAE's are achieved in one step via so called transesterification reaction. In this reaction, any fatty acid ester combined with excess of an alcohol in presence of alkali as catalyst reacts to produce a new ester compound (FAAE) comprised of the original fatty acid and the alcohol added in excess. Along with the formation of the FAAE entities, the sterols previously bound in the form of steryl esters are liberated as non-bound sterols. It should be noted that the transesterification reaction can be promoted also by an acid catalyst, though more extreme conditions are needed for significant reaction rates. In our case, the tall oil pitch stream (containing phytosterols predominantly as steryl esters) is combined with excess of low molecular weight alkyl alcohol such as methanol or ethanol and alkali as catalyst and allowed to react, where the steryl esters are transformed into the corresponding fatty acid alkyl esters and hence the bound sterols will be liberated as free sterol.

There are two major requirements towards the modified tall oil pitch which is concentrated in sterols (free and bound) and that are (i) the low acid value and (ii) the low water content (preferably water-free). The low acid value is required because if acidic functionalities are present they would be consuming the alkali catalyst and forming the corresponding salts and hence compromising the transesterification. Other possible problems in case of residual acidity and salt formation might be (a) separation issues and (b) necessity of acidulation step in order to recover the saponified acids. The residual acidity if present can be compensated by addition of extra alkali catalyst. The requirement related to the low water content is imposed since if present water promotes soap formation by the fatty acids comprising steryl esters rather than the formation of corresponding FAAE's according to the transesterification mechanism. In cases when soaps are formed instead of FAAE's, the problems mentioned for the residual acidity are applied.

According to one specific embodiment, the second process stream or phase obtained in step b), enriched in free- and bound sterols, is dehydrated prior subjecting it to transesterification conditions.

The transesterification reaction is an equilibrium reaction. The equilibrium can be shifted towards products FAAE's and free sterols through the use of excess of alkyl alcohol.

Typical alcohol excess used to promote the transesterification of the steryl esters towards FAAE's can vary from 2-20 times on molar basis relative to the steryl ester content and most preferably this excess is between 6-10 times.

As it was mentioned the preferences towards methanol and ethanol are mainly dictated by economical reasons. The additional arguments for the preferences towards methanol and ethanol are related to steric effects which are paying role during the transesterification. The transesterification involves formation of tetrahedral intermediate between the polarized steryl ester (slightly negative charge at the C centre of the carbonyl C=O group) and an electron donor such are the alkoxy (—OR) species. Such a tetrahedral intermediate is easily formed when R in the alkoxy group is small i.e. C1 or C2. As the alkoxy chain increases in length the reaction rate of transesterification drastically decreases.

According to one specific embodiment of the method according to the invention, the second process stream or phase obtained in step b), enriched in free- and bound sterols, is contacted with an amount of anhydrous methanol or ethanol prior to performing step c).

The alkali catalyst utilized to promote the transesterification is typically sodium or potassium hydroxides. Due to their solid nature, often they are dissolved firstly in the alkyl alcohol which is then combined with the sterol source stream in our case the modified tall oil pitch to affect the transesterification. The transesterification is the reaction of choice within the Biodiesel production from vegetable oils where suitable catalysts are the so called alkoxides-alkali salts of the corresponding alkyl alcohols and alkali metals. These catalysts are highly reactive and would be suitable for the transesterification of the steryl esters.

The transesterification can be promoted by heterogeneous catalyst as well. Such catalysts are for example spinel-like oxides which can be found in nature or artificially synthesized. The spinel-type oxides are combination of bivalent and trivalent oxides typically denoted by common formula MeO.Me'2O3, where Me is a bivalent ion such as calcium (II), magnesium (II), zinc (II), iron (II), manganese (II), etc. and Me' is a trivalent ion for example aluminium (III), iron (III), manganese (III), chromium (III), etc. Other type of heterogeneous catalyst is the group of the cation exchange resins in their sodium or potassium ionic forms. The advantages of utilizing a heterogeneous catalyst system are: (i) they are easy to remove from the reaction mixture; (ii) possible to recycle.

Another type of catalyst which is particularly suitable to promote the transesterification of steryl esters to the corresponding FAAE's and free sterols is so called phase-transfer catalyst. These catalysts are especially suitable for almost heterogeneous systems similar to the modified tall oil pitch-alkyl alcohol i.e. systems of very limited miscibility. The phase-transfer catalysts for cations are typically crown ether based, especially interested are their potassium forms.

To sum up, according to one specific embodiment of the present invention, the at least one catalyst used in step c) to promote transesterification is an alkali catalyst selected from the group consisting of alkali- and alkali-earth hydroxides, spinel-like oxides, alkali-forms of cation exchange resins, phase-transfer catalysts and mixtures thereof.

Intensive mixing in the CSTR, where the transesterification reaction is affected, is essential parameter that contributes to the high conversion levels of steryl esters to corresponding FAAE's and free sterols. The intensive mixing provides substantially larger contact area between the two rather non-miscible phases, namely modified tall oil pitch and alkyl alcohol.

The transesterification reaction is best affected at elevated temperatures, typically at reflux conditions. The elevated temperatures greatly increase the reaction rate. Temperatures that greatly exceed the boiling point of the alkyl alcohol can be also utilized however, in these cases the pressurized reactor is needed in order to keep the alcohol in liquid state.

Therefore, according to one specific embodiment of the present invention, the transesterification in step c) is performed in a CSTR under reflux conditions. According to yet another specific embodiment of the present invention, the transesterification in step c) is performed in a pressurized reactor at temperatures higher than 100 degrees C.

The transesterification reaction is driven up to high conversion levels of steryl esters to the corresponding FAAE's and free sterols. The conversion levels are over 80%, preferably over 90% and in some preferred embodiments are over 98%.

Upon achieving the desired conversion level with respect to the steryl esters, the reaction mixture is pumped into collective vessel where the mixture is allowed to cool-down and mature. Since the free phytosterols have limited solubility in both low molecular weight alcohol and newly formed fatty acid alkyl esters, upon cooling a crystalline phase appears in the mixture. The crystalline phase can be separated through various well-known techniques such as decantation, filtration, centrifugation, etc. to obtain a crude sterol stream and a fatty acid alkyl ester enriched stream. The crude sterol stream can be purified through a re-crystallization from a suitable solvent to obtain high quality sterol product with principle component beta-Sitosterol.

To sum up, according to one specific embodiment of the present invention, the separation of free sterols from the reaction mixture of step c) in step d) is performed by at least one of crystallization and extraction with one or more solvents. According to yet another specific embodiment of the present invention, the free sterols crystallized in the second process stream or phase obtained in step c) are separated as solid crude sterol fraction. When crystallizing, it is also possible to decant the oil and collect the crystals, to centrifuge and collect the crystals or filter the crystals after the crystallization.

The FAAE's enriched stream is subjected to conditions that promote alkyl alcohol recovery. The recovered alcohol is essentially of very high quality having in mind that TOP material does not contain any low boiling components that might be removed together with the alcohol. The recovered alcohol can be either recycled for the transesterification or utilized for the preparation of the modified TOP. The oil stream enriched in FAAE's and after the alcohol recovery may be fractionated to obtain a stream of high quality fatty acid alkyl esters. The high quality of the obtained FAAE's is due to the high temperature gap between the boiling points of the FAAE's and the remaining heavy TOP components. The obtained high quality fatty acid alkyl esters can be used as automotive fuel or formulation of such, solvent, cosmetic formulations, etc.

According to yet another embodiment of the method according to the invention, fatty acid alkyl esters are separated from the reaction mixture obtained after step d).

The invention claimed is:

1. Method for recovering phytosterols from tall oil pitch (TOP) by a sequence of reaction and separation steps, comprising the steps of:
    a) contacting TOP with a solvent comprising methanol at a temperature above 25 degrees and under 100 degrees C. thereby forming a TOP solvent mixture;
    b) separating the TOP solvent mixture, without saponification, into at least two separate process streams or phases wherein a first process stream or phase is enriched in acidic pitch components and a second process stream or phase is enriched in free sterols and bound sterols in the form of steryl esters;
    c) subjecting the second process stream or phase enriched in free sterols and steryl esters to treatment with at least one alcohol and at least one catalyst thereby forming a reaction mixture wherein at least a portion of the steryl esters is liberated as free sterols without saponification, wherein step c) is achieved by
    a transesterification promoting said steryl esters being liberated as free sterols and formation of fatty acid alkyl esters (FAAE's) corresponding to said steryl esters; and
    d) separating free sterols from the reaction mixture of step c).

2. Method in accordance with claim 1, wherein TOP is contacted with the solvent in step a) under intense mixing.

3. Method in accordance with claim 1, wherein TOP is contacted with the solvent used in step a) using at least one continuous stirred tank reactor (CSTR).

4. Method in accordance with claim 1, wherein a major portion of acidic pitch components comprising the TOP are separated based on their affinity towards polar solvents in step b).

5. Method in accordance with claim 1, wherein a major portion of acidic pitch components comprising the TOP are separated in step b) by neutralization, adsorption, extraction, distillation or combinations thereof.

6. Method in accordance with claim 1, wherein the contact of TOP with the solvent in step a) and the separation of TOP into two process streams or phases in step b) are performed in a mixer settler.

7. Method in accordance with claim 1, wherein the acidic pitch components of the TOP are separated by at least one extraction with solvent in steps a) and b).

8. Method in accordance with claim 1, wherein the second stream or phase obtained in step b), enriched in free- and bound sterols, has an acid value below 1 mg KOH $g^{-1}$.

9. Method in accordance with claim 1, wherein the free sterols crystallized in the second process stream or phase obtained in step c) are separated as solid crude sterol fraction.

10. Method in accordance with claim 1, wherein the second process stream or phase obtained in step b), enriched in free- and hound sterols, is dehydrated prior transesterification in step c).

11. Method in accordance with claim 1, wherein the second process stream or phase obtained in step b), enriched in free- and bound sterols, is contacted with an amount of anhydrous methanol or ethanol prior to performing step c).

12. Method in accordance with claim 1, wherein the transesterification in step c) is performed in a CSTR under reflux conditions.

13. Method in accordance with claim 1, wherein the at least one catalyst used in step c) is used to promote transesterification and is an alkali catalyst selected from the group consisting of alkali- and alkali-earth hydroxides, spinel-like oxides, alkali-forms of cation exchange resins, phase-transfer catalysts and mixtures thereof.

14. Method in accordance with claim 1, wherein the separating of free sterols from the reaction mixture of step c) in step d) is performed by at least one of crystallization and extraction with one or more solvents.

15. Method in accordance with claim 1, wherein fatty acid alkyl esters are separated from the reaction mixture obtained after step d).

16. Method in accordance with claim 1, wherein free sterols that have crystallized within the second process stream or phase after step b) are separated from the second process stream or phase before step c).

* * * * *